(12) United States Patent
Furrer et al.

(10) Patent No.: US 11,860,176 B2
(45) Date of Patent: Jan. 2, 2024

(54) METHOD OF OPERATING AN ANALYTICAL LABORATORY

(71) Applicant: Roche Diagnostics Operations, Inc., Indianapolis, IN (US)

(72) Inventors: Frederic Furrer, Schwarzenbach (CH); Marco Maetzler, Belmont, CA (US)

(73) Assignee: Roche Diagnostics Operations, Inc, Indianapolis, IN (US)

( * ) Notice: Subject to any disclaimer, the term of this patent is extended or adjusted under 35 U.S.C. 154(b) by 0 days.

(21) Appl. No.: 17/699,514

(22) Filed: Mar. 21, 2022

(65) Prior Publication Data
US 2022/0206023 A1 Jun. 30, 2022

Related U.S. Application Data

(63) Continuation of application No. 17/082,405, filed on Oct. 28, 2020, now Pat. No. 11,313,870.

(30) Foreign Application Priority Data

Oct. 31, 2019 (EP) ..................................... 19382952

(51) Int. Cl.
*G01N 35/00* (2006.01)
(52) U.S. Cl.
CPC ... *G01N 35/0092* (2013.01); *G01N 35/00871* (2013.01)
(58) Field of Classification Search
CPC ............. G16H 10/40; G01N 35/00871; G01N 2035/0094; G01N 35/0092
See application file for complete search history.

(56) References Cited

U.S. PATENT DOCUMENTS

| 5,366,896 | A | 11/1994 | Margrey et al. |
| 8,329,103 | B2 * | 12/2012 | Wakamiya ......... G01N 35/0092 |
| | | | 422/67 |
| 9,097,689 | B2 | 8/2015 | Yamato et al. |

(Continued)

FOREIGN PATENT DOCUMENTS

| EP | 1870825 A1 | 12/2007 |
| WO | 2001/009618 A1 | 2/2001 |
| WO | 2017/205748 A1 | 11/2017 |

*Primary Examiner* — Shogo Sasaki
(74) *Attorney, Agent, or Firm* — Roche Diagnostics Operations, Inc.

(57) ABSTRACT

A method of operating an analytical laboratory is presented. The method comprises the steps of: setting a load limit for each laboratory instrument at maximum instrument capacity; dispatching biological samples to laboratory instrument(s) at a dispatch rate not greater than the instrument load limit; each laboratory instrument sending test order queries to the laboratory middleware upon identifying a biological sample; in response to the test order queries transmitting test orders to the laboratory instruments corresponding to the biological samples; the laboratory middleware monitoring a query rate of the plurality of laboratory instruments in order to determine an effective flow rate corresponding to each laboratory instrument; decreasing the load limit of a first laboratory instrument if its effective flow rate is lower than the dispatch rate; increasing the load limit for the first laboratory instrument if its effective flow rate is greater than or equal to the dispatch rate.

20 Claims, 10 Drawing Sheets

(56) References Cited

U.S. PATENT DOCUMENTS

| | | | |
|---|---|---|---|
| 2006/0178776 A1* | 8/2006 | Feingold | G16H 40/63 |
| | | | 700/245 |
| 2008/0312893 A1 | 12/2008 | Denton | |
| 2009/0081794 A1 | 3/2009 | Wakamiya et al. | |
| 2009/0206234 A1* | 8/2009 | Okuda | G01N 15/1456 |
| | | | 250/201.2 |
| 2014/0342465 A1 | 11/2014 | Haechler et al. | |

* cited by examiner

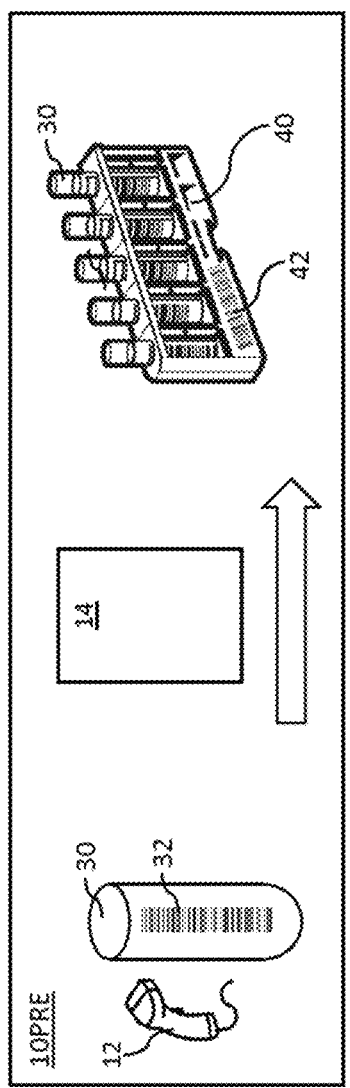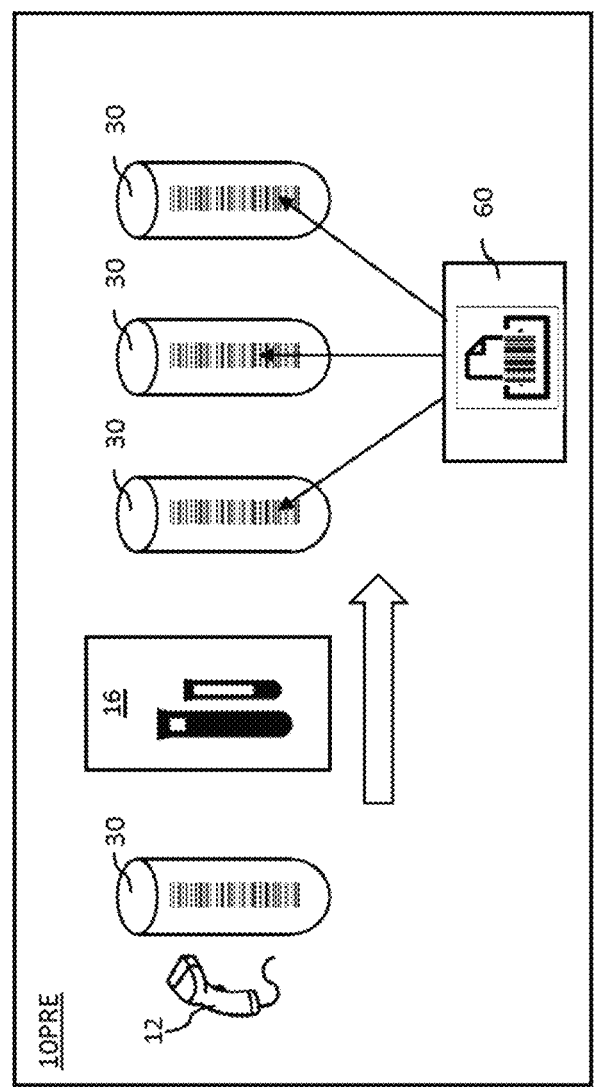

METHOD OF OPERATING AN ANALYTICAL LABORATORY

CROSS-REFERENCE TO RELATED APPLICATIONS

This application is a continuation of U.S. application Ser. No. 17/082,405, filed Oct. 28, 2020, now U.S. patent Ser. No. 11/313,870, which claims priority to EP 19382952.0, filed Oct. 31, 2019, which are hereby incorporated by reference.

BACKGROUND

The present disclosure generally relates to a computer-implemented method of operating an analytical laboratory, in particular an in-vitro diagnostic laboratory, and to an analytical laboratory configured to carry out the disclosed method.

In vitro diagnostic testing has a major effect on clinical decisions, providing physicians with pivotal information. In analytical laboratories, in particular, in-vitro diagnostic laboratories, a multitude of analyses on biological samples are executed by laboratory instruments in order to determine physiological and biochemical states of patients, which can be indicative of a disease, nutrition habits, drug effectiveness, organ function and the like.

According to established laboratory procedures in complex analytical laboratories, a plurality of instruments process biological samples according to test orders, each test order defining one or more processing steps to be carried out on the biological sample. After the biological sample has been received and identified by a pre-analytical laboratory instrument, a laboratory middleware retrieves the corresponding test orders and determines which instruments are required to process the biological sample according to the test order(s). Having identified the required instrument(s), the laboratory middleware determines a sample workflow for each sample according to the test order(s). The sample workflow comprises a sequence and/or timing of carrying out the one or more test orders by the one or more analytical instruments.

In known analytical laboratories, the laboratory middleware determines the sample workflow based on a load limit for each laboratory instrument based on a maximum instrument capacity.

The maximum instrument capacity is either set by the manufacturer/provider of the respective instrument or determined based on historical data reflecting the (average/mean) performance of the instrument. The load limit, instrument capacity as well as the flow rate of an instrument is defined as the number of biological samples the respective instrument is able to process in a given time frame (e.g., per hour, per day, etc.). Alternatively, this is referred to as processing rate/frequency or instrument throughput and the like However, it has been observed that the performance of laboratory instruments sometimes deviates (significantly) from the maximum instrument capacity. Such deviations have various causes, such as (un) availability of instrument consumables, degradation/wear of certain components of the instrument; unfavorable environmental conditions; necessity of more frequent calibration/quality control procedures and/or overloading of the laboratory instruments with biological samples at rates higher than their current capacity.

Degradation in the performance of laboratory instruments and hence deviations from the assumed instrument capacity leads to situations where analytical laboratories operate using the wrong "assumptions" of instrument capacity, leading to overloading and/or unfavorable balancing of the load between laboratory instruments. Even if the load limit for each laboratory instrument is revised on a regular basis, deviations of the performance of laboratory instruments may not be reacted upon in a timely manner in known analytical laboratories, potentially leading to overloading/underutilization of laboratory instruments.

Hence, there is a need for an analytical laboratory and a method of operating an analytical laboratory, which prevents overloading/underutilization of laboratory instruments.

Furthermore, it has been observed that even if one would assume a theoretically perfect load distribution between laboratory instruments in an analytical laboratory, without some control of the "input" of the analytical laboratory as a whole, there would still be a risk that the analytical laboratory would become overloaded if the inflow of biological samples is higher than the overall processing capacity.

Hence, there is a further need for an analytical laboratory and a method of operating an analytical laboratory wherein an overloading of the analytical laboratory is prevented.

At a certain point, an overloaded analytical laboratory is unable to receive additional biological samples. This is particularly problematic with respect to biological samples which need to be processed urgently (e.g., from emergency care or other situations where e.g., a life-critical decision is dependent on the timely availability of the corresponding test results).

Therefore, there is an even further need for an analytical laboratory and method of operating an analytical laboratory, which enables timely receipt, and processing of urgent samples, irrespective of overall load of the analytical laboratory.

SUMMARY

According to the present disclosure, an analytical system and method of operating an analytical laboratory comprising a laboratory middleware communicatively connected to a plurality of laboratory instruments configured to process biological samples is presented. The method can comprise the steps of setting a load limit by the laboratory middleware for each laboratory instrument at a value equal to a maximum instrument capacity of the laboratory instrument and dispatching biological samples by the laboratory middleware to laboratory instrument(s) at a dispatch rate not greater than the instrument load limit. The biological samples can be dispatched to laboratory instrument(s) configured to carry out at least one test order corresponding to the biological sample. The method can also comprise receiving and identifying biological samples by the laboratory instruments and sending test order queries by each laboratory instrument to the laboratory middleware upon identifying a biological sample. The test order query can comprise data identifying the biological sample. The method can also comprise, in response to the test order queries, transmitting test orders by the laboratory middleware to the laboratory instruments corresponding to the biological samples identified in the test order queries, monitoring a query rate of the plurality of laboratory instruments by the laboratory middleware in order to determine an effective flow rate corresponding to each laboratory instrument, decreasing the load limit by the laboratory middleware of a first laboratory instrument of the plurality of laboratory instruments if the effective flow rate of the first laboratory instrument is lower than the dispatch rate to the first laboratory instrument, and increasing the load limit by the laboratory middleware for the first laboratory instrument if the effective flow rate of the first laboratory instrument is greater than or equal to the dispatch rate to the first laboratory instrument Accordingly, it is a feature of the embodiments of the present disclosure to address the need for an analytical laboratory and method of operating an analytical laboratory which prevents overloading/underutilization of laboratory instruments by determining an effective flow rate of the laboratory instruments and dynamically reacting to the deviations of the effective flow rate by controlling the load limit of each instrument. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 6 illustrates a highly schematic block diagram of a pre-analytical laboratory instrument of the disclosed laboratory system according to an embodiment of the present disclosure.

FIG. 7 illustrates a highly schematic block diagram of a pre-analytical laboratory instrument of the disclosed laboratory system according to an embodiment of the present disclosure.

DETAILED DESCRIPTION

Figure 1:
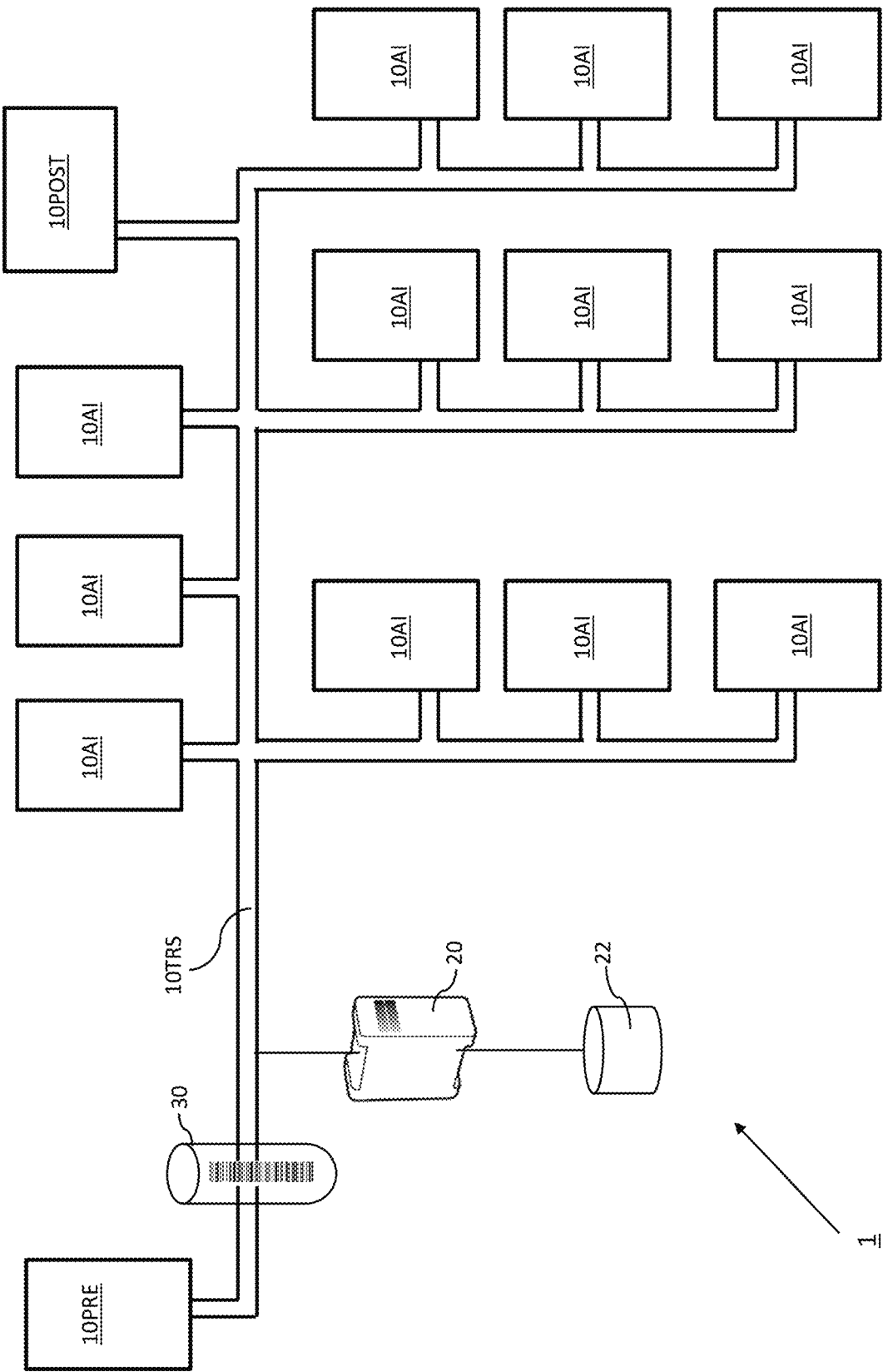
FIG. 1 illustrates a highly schematic block diagram of the analytical laboratory according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Certain terms will be used in this patent application, the formulation of which should not be interpreted to be limited by the specific term chosen, but as to relate to the general concept behind the specific term.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term 'analyte' can relate to a component of a sample to be analyzed, e.g., molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence, absence and/or concentration is intended. Examples of analytes are e.g., glucose, coagulation parameters, endogenic proteins (e.g., proteins released from the heart muscle), metabolites, nucleic acids and so on.

The term 'analysis or 'analytical test' as used herein can encompass a laboratory procedure characterizing a parameter of a biological sample for qualitatively assessing or quantitatively measuring the presence or amount or the functional activity of an analyte.

The term 'reagent' as used herein can refer to materials necessary for performing an analysis of analytes, including reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The terms 'sample container', 'sample holder' and 'sample tube' can refer to any individual container for storing, transporting, and/or processing a sample. In particular, the term without limitation can refer to a piece of laboratory glass- or plastic-ware optionally comprising a cap on its upper end. The container can comprise an opening for dispensing/aspirating liquid into or out of the vessel. The opening may be closed by a cap, a breakable seal or like suitable means for closing the opening in a liquid-tight manner. Sample tubes, e.g., sample tubes used to collect blood, often comprise additional substances such as clot activators or anticoagulant substances, which can have an impact on the processing of the sample. Consequently, different tube types typically can be adapted for pre-analytical and analytical requirements of a particular analysis, e.g., a clinical chemistry analysis, a hematological analysis or a coagulation analysis. A mix up of sample tube types can make samples unusable for analysis. To prevent errors in the collection and handling of samples, the sample caps of many tube manufacturers can be encoded according to a fixed and uniform color scheme. Some sample tubes types, in addition, or alternatively, can be characterized by particular tube dimensions, cap dimensions, and/or tube color. A dimension of a tube can comprises e.g., its height, its size and/or further characteristic shape properties. Sample containers can be identified using identification tag(s) attached thereto. The term 'identification tag' as used herein can refer to an optical and/or radio frequency based identifier that allows the identifier tag to be uniquely identified by a corresponding identification tag reader.

The 'identification tag' shall comprise—but is not limited to—a barcode, a quick response (QR) code or a radio frequency identification (RFID) tag.

The term 'sample carrier' as used herein can refer to any kind of holder configured to receive one or more sample tubes and configured to be used for transporting sample tube(s).

Sample carriers may be of two major types, single holders and sample racks.

A 'single holder' can be a type of sample carrier configured to receive and transport a single sample tube. Typically, a single holder can be provided as a puck, i.e., a flat cylindrical object with an opening to receive and retain a single sample tube.

A 'sample rack' can be a type of sample carrier, typically made of plastics and/or metal, adapted for receiving, holding and transporting a plurality of sample tubes, e.g., five or more sample tubes e.g., disposed in one or more rows. Apertures, windows or slits may be present to enable visual or optical inspection or reading of the sample tubes or of the samples in the sample tubes or of a label, such as a barcode, present on the sample tubes held in the sample rack.

The term 'laboratory instrument' as used herein can encompass any apparatus or apparatus component operable to execute one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments as well as analytical instruments.

The term 'analyzer'/'analytical instrument' as used herein can encompass any apparatus or apparatus component configured to obtain a measurement value. An analyzer can be operable to determine via various chemical, biological, physical, optical or other technical procedures a parameter value of the sample or a component thereof. An analyzer may be operable to measure said parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent-holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzers are clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'pre-analytical instrument' as used herein can encompass any apparatus or apparatus component that can be configured to perform one or more pre-analytical processing steps/workflow steps comprising—but not limited to—centrifugation, resuspension (e.g., by mixing or vortexing), capping, decapping, recapping, sorting, tube type identification, sample quality determination and/or aliquotation steps. The processing steps may also comprise adding chemicals or buffers to a sample, concentrating a sample, incubating a sample, and the like.

The term 'post-analytical instrument' as used herein can encompass any apparatus or apparatus component that can be configured to perform one or more post-analytical processing steps/workflow steps comprising—but not limited to—sample unloading, transport, recapping, decapping, temporary storage/buffering, archiving (refrigerated or not), retrieval and or disposal.

The term 'sample transportation system' as used herein encompasses any apparatus or apparatus component that is configured to transport sample carriers (each holding one or more sample containers) between laboratory instruments. In particular, the sample transportation system is a one dimensional conveyor-belt based system, a two-dimensional transportation system (such as a magnetic sample carrier transport system) or a combination thereof.

The term 'laboratory middleware' as used herein can encompass any physical or virtual processing device configurable to control a laboratory instrument/or system comprising one or more laboratory instruments in a way that workflow(s) and workflow step(s) can be conducted by the laboratory instrument/system. The laboratory middleware may, for example, instruct the laboratory instrument/system to conduct pre-analytical, post analytical and analytical workflow(s)/workflow step(s). The laboratory middleware may receive information from a data management unit regarding which steps need to be performed with a certain sample. In some embodiments, the laboratory middleware might be integral with a data management unit, may be comprised by a server computer and/or be part of one laboratory instrument or even distributed across multiple instruments of the analytical laboratory. The laboratory middleware may, for instance, be embodied as a programmable logic controller running a computer-readable program provided with instructions to perform operations.

A 'data storage unit' or 'database' can be a computing unit for storing and managing data such as a memory, hard disk or cloud storage. This may involve data relating to biological sample(s) to be processed by the automated system. The data management unit may be connected to an LIS (laboratory information system) and/or an HIS (hospital information system). The data management unit can be a unit within or co-located with a laboratory instrument. It may be part of the laboratory middleware. Alternatively, the database may be a unit remotely located. For instance, it may be embodied in a computer connected via a communication network.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

An 'analytical laboratory' as used herein can comprise a laboratory middleware operatively coupled to one or more analytical; pre- and post-analytical laboratory instruments wherein the laboratory middleware can be operable to control the instruments. In addition, the laboratory middleware may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for said analysis and the like. In particular, the instruments of an analytical laboratory and the laboratory middleware can be interconnected by a communication network.

A 'test order' as used herein can encompass any data object, computer loadable data structure, modulated data representing such data being indicative of one or more processing steps to be executed on a particular biological sample. For example, a test order may be a file or an entry in a database. A test order can indicate an analytical test if, for example, the test order can comprise or can be stored in association with an identifier of an analytical test to be executed on a particular sample.

A 'STAT sample'/'urgent sample' can be a sample which can need to be processed and analyzed very urgently as the analysis result may be of life-crucial importance for a patient. STAT or urgent samples can be identified either by data stored on an identifier tag attached to a sample container holding the biological sample and/or by data comprised by and/or associated with the test order indicative of an urgency/priority level of the respective test order. The urgency/priority level of a test order may be indicated as binary option (e.g., urgent respectively normal) and/or as a scale (e.g., 10 very urgent, 7 normal, 5 least urgent test order). Additionally, or alternatively, a STAT/urgent sample may be identified by a particular type of sample container, by a particular type of sample container cap, by a particular color of sample container cap and/or a particular type/color/format of an identifier tag attached to the sample container.

Embodiments herein disclosed can address the need for an analytical laboratory and a method of operating an analytical laboratory, which can prevent overloading/underutilization of laboratory instruments by determining an effective flow rate of the laboratory instruments and dynamically reacting to the deviations of the effective flow rate by controlling the load limit of each instrument.

Embodiments of the disclosed computer implemented method of operating an analytical laboratory comprising a laboratory middleware communicatively connected to a plurality of laboratory instruments configured to process biological samples can comprise the steps of setting a load limit for each laboratory instrument at a value equal to a maximum instrument capacity of the respective laboratory instrument by the laboratory middleware and dispatching biological samples to laboratory instrument(s) at a dispatch rate not greater than the instrument load limit by the laboratory middleware. The biological samples can be dispatched to those laboratory instrument(s), which can be configured to carry out at least one test order corresponding to the respective biological sample. The method can also comprise the steps of receiving and identifying biological samples by the laboratory instruments and, upon identifying a biological sample, sending test order queries to the laboratory middleware by each laboratory instrument. The test order query(s) comprising data identifying the biological sample. In response to the test order queries, the laboratory middleware can transmit test orders to the laboratory instruments corresponding to the biological samples identified in the respective test order queries.

According to some embodiments disclosed herein, the laboratory middleware can retrieve the test orders corresponding to a biological sample from a data storage unit based on said data identifying the biological sample. The laboratory middleware can monitor a query rate of the plurality of laboratory instruments in order to determine an effective flow rate corresponding to each laboratory instrument.

The query rate can be defined as a number of distinct test order queries received from a particular laboratory instruments in a set period of time, such as per minute, hour, and so on. Since the laboratory instruments send the test queries at a time when they are ready to process the biological sample(s), the query rate can be a good indication of the effective processing capacity of the respective laboratory instrument at that time.

If the effective flow rate of the first laboratory instrument is lower than the dispatch rate to the first laboratory instrument, the laboratory middleware can decrease the load limit of a first laboratory instrument of the plurality of laboratory instruments. The load limit can be decreased to ensure that no backlog of unprocessed samples accumulates at the laboratory instrument, causing even further overloading of the instrument.

On the other hand, if the effective flow rate of the first laboratory instrument is greater than or equal to the dispatch rate to the first laboratory instrument, the laboratory middleware can increase the load limit for the first laboratory instrument.

Embodiments disclosed herein can be advantageous since adjusting the load limit of laboratory instruments as a reaction to their effective flow rate can avoid overloading, or underutilization. Furthermore, determining the effective flow rate by the laboratory middleware based on the test order queries received from the laboratory instruments can be advantageous as it can be devoid of any assumptions of performance and can be implemented even without any change to the existing laboratory instruments.

According to further embodiments disclosed herein, the laboratory middleware can increase or decrease the load limit of the first laboratory instrument using continuously modulated control such as, for example, a proportional-integral-derivative PID, a proportional-integral PI, a proportional-derivative PD, a proportional or an integral control algorithm. Such embodiments can be particularly advantageous since continuously modulated control can be configured to keep the effective flow rate as close as possible to the maximum instrument capacity, quickly reacting to deviations without overreacting.

In addition to controlling (i.e. increasing or decreasing) the load limit, further embodiments disclosed herein can react to deviations of the effective flow rate from the dispatch rate by performing load balancing between laboratory instruments and/or buffering biological sample(s) to temporarily reduce the load on an otherwise overloaded instrument.

Further embodiments disclosed herein can address the further need for an analytical laboratory and method of operating an analytical laboratory wherein an overloading of the entire analytical laboratory can be prevented. As mentioned above, even if one would assume a theoretically perfect load distribution between laboratory instruments in an analytical laboratory, without some control of the input of the analytical laboratory as a whole, there can still be a risk that the analytical laboratory can become overloaded if the inflow of biological samples is higher than the overall processing capacity. Therefore, embodiments disclosed herein addressing this issue can further comprise the step of masking one or more of the plurality of laboratory instruments, wherein masking can comprise preventing one or more of the plurality of laboratory instruments from receiving biological sample(s), in particular biological sample(s) having at least one associated test order which the first laboratory instrument is configured to carry out. According to embodiments disclosed herein, preventing one or more of the plurality of laboratory instruments from receiving biological sample(s) can comprise preventing (physically) even the loading of the respective biological sample(s) and/or automatically unloading the biological sample(s), e.g., into an error output. Such embodiments can be advantageous as they can limit the inflow of biological samples into the analytical laboratory, thereby preventing that the overall analytical laboratory is overloaded, including buffer and archiving capacity of the laboratory instruments.

Further embodiments disclosed herein can relate to ensuring the analytical laboratory can still receive and process urgent biological samples while still controlling the overall load of the analytical laboratory. In order to achieve this, according to further embodiments, masking of laboratory instruments can be performed with respect to all laboratory instruments, other than one or more laboratory instruments reserved for receiving biological samples of high priority.

Referring initially to FIG. 1, FIG. 1 shows a highly schematic block diagram of an embodiment of the disclosed analytical laboratory 1. As shown on the block diagram of FIG. 1, embodiments of the disclosed analytical laboratory 1 for processing biological sample(s) can comprise a plurality of laboratory instruments 10AI, 10PRE, 10POST and a laboratory middleware 20 communicatively connected by a communication network. The plurality of laboratory instruments 10AI, 10PRE, 10POST can be configured to execute processing steps on the biological samples according to instructions from the laboratory middleware 20. All laboratory instruments 10AI, 10PRE, 10POST can be collectively referred to using the reference numeral 10.

The pre-analytical instruments 10PRE comprised by the analytical laboratory 1 may be one or more from the list comprising: an instrument for centrifugation of samples, a capping-, decapping- or recapping instrument, aliquoter, a buffer to temporarily store biological samples or aliquots thereof.

The post-analytical instruments 10POST comprised by the analytical laboratory 1 may be one or more from the list comprising: a recapper, an unloader for unloading a sample from an analytical system and/or transporting the sample to a storage unit or to a unit for collecting biological waste.

According to various embodiments of the disclosed analytical laboratory 1, the plurality of laboratory instruments 10AI, 10PRE, 10POST may be identical or different instruments such as clinical- & immunochemistry analyzers, coagulation chemistry analyzers, immunochemistry analyzers, urine analyzers, nucleic acid analyzers, hematology instruments and the like.

The laboratory middleware 20 can be configured to control the analytical laboratory 1 to carry out the steps of one or more of the methods herein disclosed and can be communicatively connected to the data storage unit 22.

As shown on FIG. 1, the analytical laboratory 1 can further comprise a sample transportation system 10TRS interconnecting the plurality of laboratory instruments 10AI, 10PRE, 10POST. According to embodiments disclosed herein, the sample transportation system 10TRS can be a one-dimensional conveyor-belt based system. According to further embodiments disclosed (but not illustrated), the sample transportation system 10TRS can be a two-dimensional transportation system (such as a magnetic sample carrier transport system). The analytical laboratory 1 can be configured to carry out the method according to the embodiments disclosed herein.

Turing now to FIGS. 2-5, embodiments of the disclosed method of operating an analytical laboratory shall be described with reference to the figures.

Figure 2:
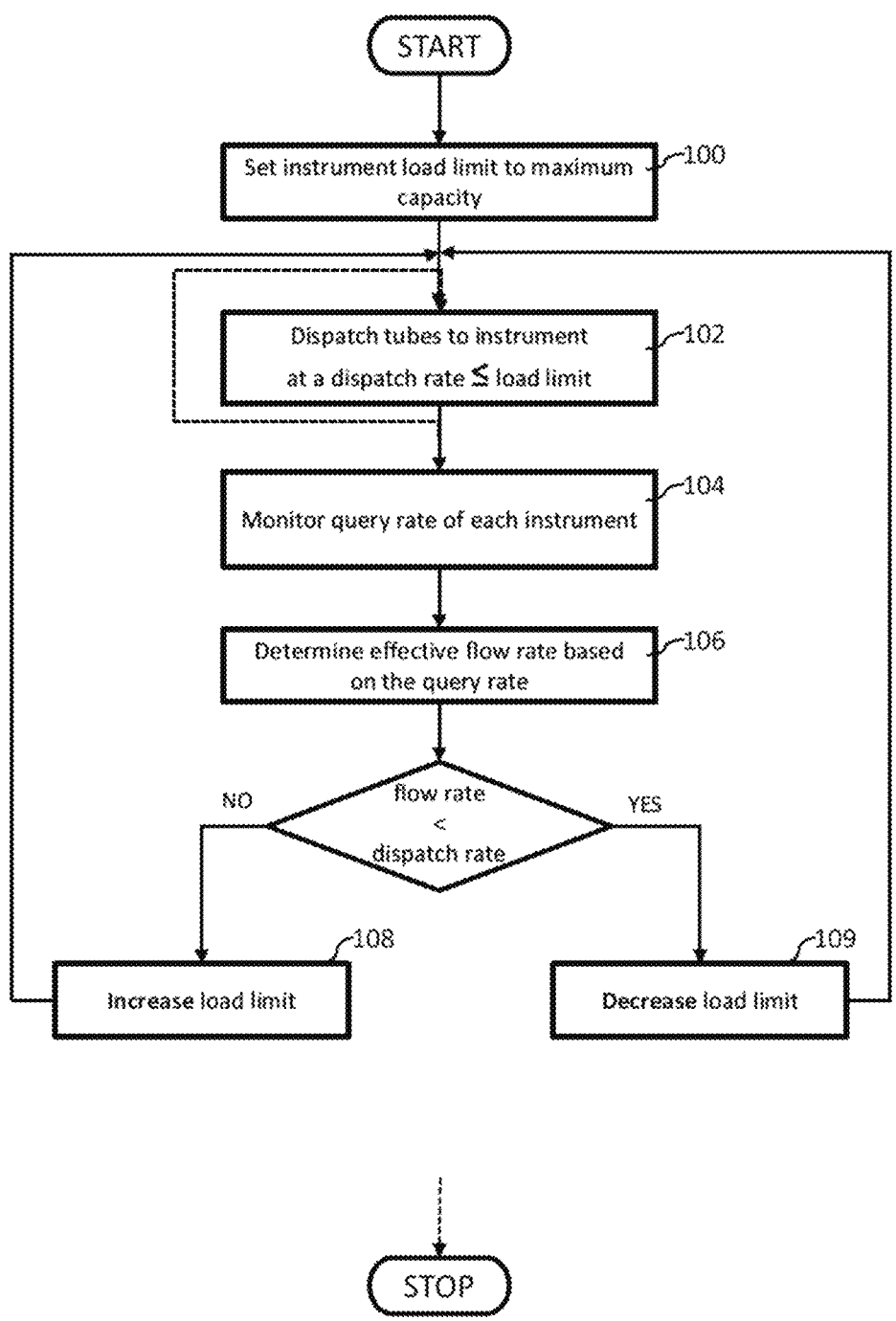
FIG. 2 illustrates a flowchart illustrating a method of operating an analytical laboratory according to an embodiment of the present disclosure.

As shown on FIG. 2, in a first preparatory step 100, a load limit can be set for each laboratory instrument 10. The load limit can initially be set at a value equal to a maximum instrument capacity of the respective laboratory instrument 10. According to embodiments disclosed herein, the maximum instrument capacity can be set by a vendor, manufacturer, and/or operator, optionally considering a safety margin. The maximum instrument capacity as well as the load limit may be expressed as a number of biological samples a laboratory instrument 10 can process in a given time frame, such as, for example, samples per hour/day and the like. Achieving an effective processing rate of the laboratory instruments 10 as close as possible to the maximum instrument capacity is the goal of the optimization by the laboratory middleware 20.

Once the load limit is set, in step 102, the laboratory middleware 20 can dispatch biological samples to laboratory instrument(s) 10 at a dispatch rate not greater than the instrument load limit. If the number of biological sample(s) in the analytical laboratory 1 overall that need processing by the respective laboratory instrument 10 is lower than the load limit, then, of course, the laboratory middleware 20 can dispatch biological sample(s) at a rate lower than the load limit. The biological samples can be dispatched to those laboratory instrument(s) 10, which are configured to carry out at least one test order corresponding to the respective biological sample. Additionally, according to embodiments disclosed herein, the laboratory middleware 20 can check whether respective laboratory instrument 10 has all resources (such as consumables, reagents, quality control) available and ready to process the biological sample according to the corresponding test order.

Thereafter, not illustrated on the flowchart of FIG. 2 for clarity, the laboratory instruments 10 can receive and identify the biological sample(s) dispatched thereto. Upon identifying the biological samples, each laboratory instrument 10 can send test order queries to the laboratory middleware 20, the test order query comprising data identifying the biological sample. In other words, the laboratory instruments 10 can ask the laboratory middleware what test to perform on the received biological sample(s). In response to the test order queries, the laboratory middleware 20 can transmit test orders to the laboratory instruments 10 corresponding to the biological samples identified in the respective test order queries. A test order can comprise data indicative of one or more processing steps to be carried out on the biological sample. According to embodiments disclosed herein, the test orders can be retrieved from a data storage 22 such as, for example, a database internal or communicatively connected to the laboratory middleware 20.

The laboratory instruments 10 can then process the biological sample(s) according to the test orders sent to them by the laboratory middleware 20.

The sequence of the laboratory instruments 10 receiving/identifying biological samples and querying the laboratory middleware 20, the laboratory middleware 20 replying with the test order, and the laboratory instruments 10 processing the biological samples can be repeated in the analytical laboratory 1.

Parallel thereto, in a step 104, the laboratory middleware 20 can monitor the rate at which the plurality of laboratory instruments 10 query the laboratory middleware 20 for test orders (referred to hereafter as query rate). Since the laboratory instruments 10 cannot process biological samples without a test order, the query rate can be a direct and reliable indication of the rate at which the laboratory instrument 10 processes biological samples at a given time. Hence, by monitoring the query rate, in a step 106, the laboratory middleware 20 can determine an effective flow rate corresponding to each laboratory instrument 10, the effective flow rate being indicative of the rate at which the laboratory instrument 10 processes biological samples.

The laboratory middleware 20 can then compare the effective flow rate of each laboratory instrument 10 with the dispatch rate of biological samples to that laboratory instrument 10 (referred to hereafter as first laboratory instrument 10). If the effective flow rate of a first laboratory instrument 10 is lower than the dispatch rate to the first laboratory instrument 10, the laboratory middleware 20, in a step 109, can decrease its load limit (of the first laboratory instrument 10). In other words, if the laboratory middleware 20 determines that the first laboratory instrument 10 is not able to process its workload (dispatched samples), it can reduce its load limit to avoid overloading the instrument.

On the other hand, if the effective flow rate of the first laboratory instrument 10 is greater than or equal to the dispatch rate to the first laboratory instrument 10, the laboratory middleware 20, in a step 108, can increase the load limit for the first laboratory instrument 10.

The method and the system disclosed herein can be advantageous since adjusting the load limit of laboratory instruments 10 as a reaction to their effective flow rate can avoid overloading, or underutilization. Furthermore, determining the effective flow rate by the laboratory middleware based on the test order queries received from the laboratory instruments 10 can be advantageous as it can be devoid of any assumptions of performance and can be implemented even without any change to the existing laboratory instruments 10.

Some embodiments of how the middleware 20 can determine the amount the load limit can be increased/decreased will be described with reference to the sequence of FIGS. 3A-C.

Figure 3A:
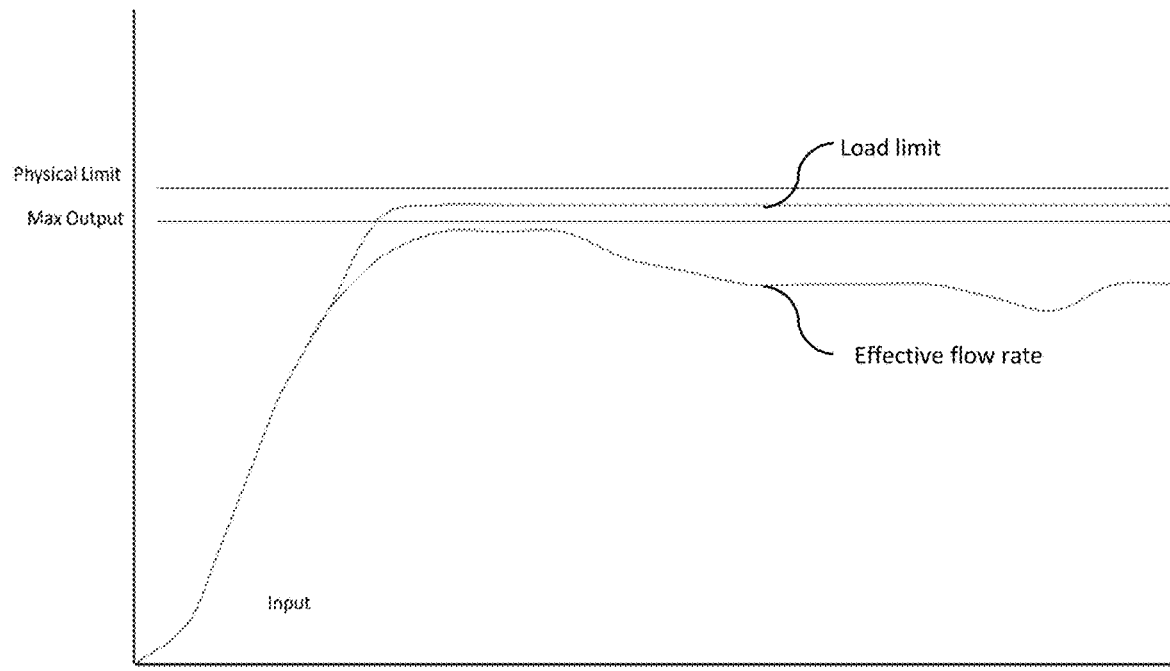
FIGS. 3A-3B illustrate a set of diagrams illustrating instrument processing rates and load limits according to an embodiment of the present disclosure.

FIG. 3A shows a simulation of a current prior art performance in one particular scenario where a laboratory instrument is processing biological samples at its maximum instrument capacity for a considerable amount of time. The line 310 illustrates the dispatch rate to the laboratory instrument. The line 320 illustrates the effective flow rate of the laboratory instrument.

The horizontal lines correspond to theoretical and physical limits of such laboratory instruments. With the current prior art laboratory middleware, the performance output (effective flow rate) would become degraded over time because the laboratory instruments are sometimes not able to process biological samples at such a constant dispatch rate. This situation can become even more critical when a laboratory instrument needs to be temporarily stopped (for replacing a reagent cassette for example), since biological samples would accumulate and a backlog would arise, which could overload the laboratory instrument.

Figure 3B:
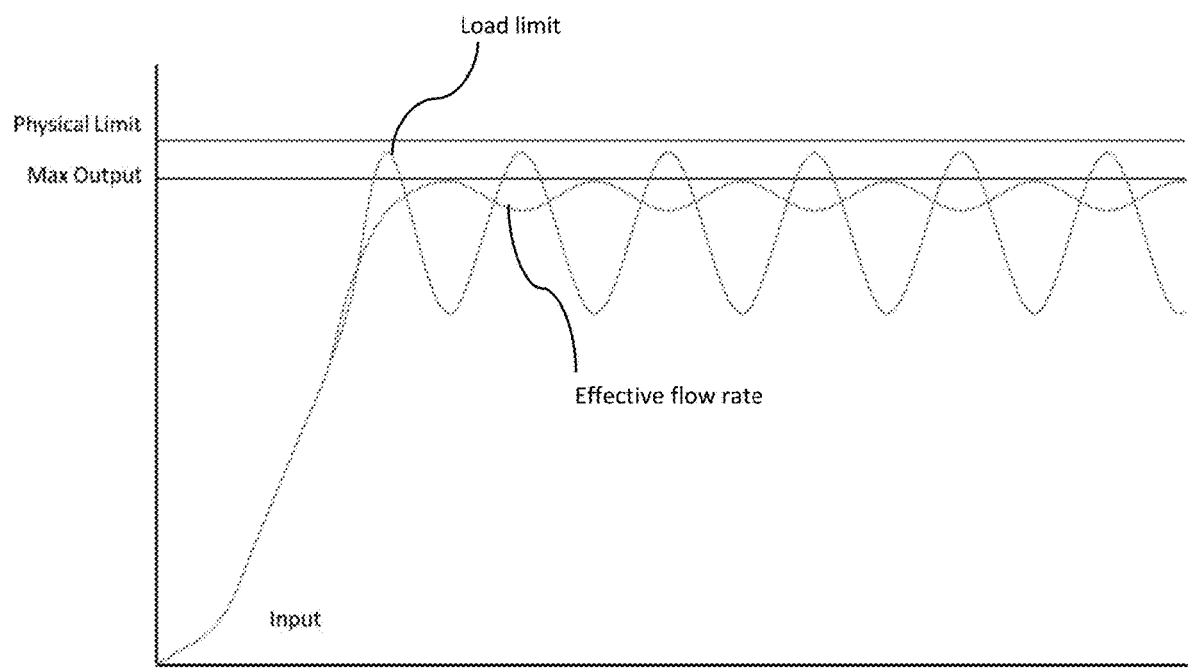

FIG. 3B, shows the effect of the disclosed method comprising increasing respectively decreasing the load limit of a laboratory instrument 10 as a reaction to its effective flow rate. As illustrated in this figure, proactively decreasing the load limit of an instrument can prevent overloading, allowing the instrument to return closer to its maximum capacity. On the other hand, increasing the load limit once the instrument is again able to process samples at the rate they are dispatched can prevent underutilization of the instrument.

According to embodiments disclosed herein, the laboratory middleware 20 can increase or decrease the load limit of the first laboratory instrument 10 using continuously modulated control such as, for example, a proportional-integral-derivative PID, a proportional-integral PI, a proportional-derivative PD, a proportional or an integral control algorithm. A continuously modulated control continuously (or quasi-continuously) can calculate an error value e(t) as the difference between a desired set point (SP) and a measured process variable (PV) and can apply a correction based on proportional, integral, and derivative terms (denoted P, I, and D respectively). The error value e can be calculated by the laboratory middleware 20 as the difference between the effective flow rate and the maximum instrument capacity. From the variation of the error value e over time, an error curve e(t) can be determined.

In order to bring the effective flow rate of a laboratory instrument as close as possible to its maximum instrument capacity, the laboratory middleware 20 can increase/decrease the load limit by a correction value determined as a weighted sum of:

A proportional term P—The proportional term P can be calculated as proportional to the error value e and can be indicative of the magnitude of the error value e. The proportional response can be adjusted by multiplying the error by a proportional gain.

An integral term I—The integral term I can be calculated as an integral of the error curve e(t) over a period of time t and can be indicative of the magnitude and duration of the error value e. In other words, the contribution from the integral term I can be proportional to both the magnitude of the error value e and the duration of the error value e. The integral in a PID controller can be the sum of the instantaneous error over time and gives the accumulated offset that should have been corrected previously. The accumulated error can then be multiplied by the integral gain and added to the controller output. The advantage of the integral term I can be that it can accelerate the return of the performance (effective flow rate) of the process towards its target (maximum instrument capacity) and can eliminate the residual steady-state error that occurs with a pure proportional controller.

A derivative term D—The derivative term D can be calculated as a derivative of the error curve e(t) over a period of time t and can be indicative of a rate of change of the error value e. The derivative of the process error can be calculated by determining the slope of the error over time and multiplying this rate of change by the derivative gain. The magnitude of the contribution of the derivative term D to the overall control action is termed the derivative gain. Derivative action can predict system behavior and thus can improve settling time and stability of the system.

It can be noted that according to particular embodiments, one or more of the proportional gain; the integral gain; and/or the derivative gain may be also zero. According to further embodiments disclosed herein, the one or more of the proportional gain; the integral gain; and/or the derivative gain can be refined in view of the response of the system, namely the change of effective flow rate as a response to a change in the load limit.

Turning now to FIGS. 4A-D, further embodiments of the disclosed method will be described.

Figure 4A:
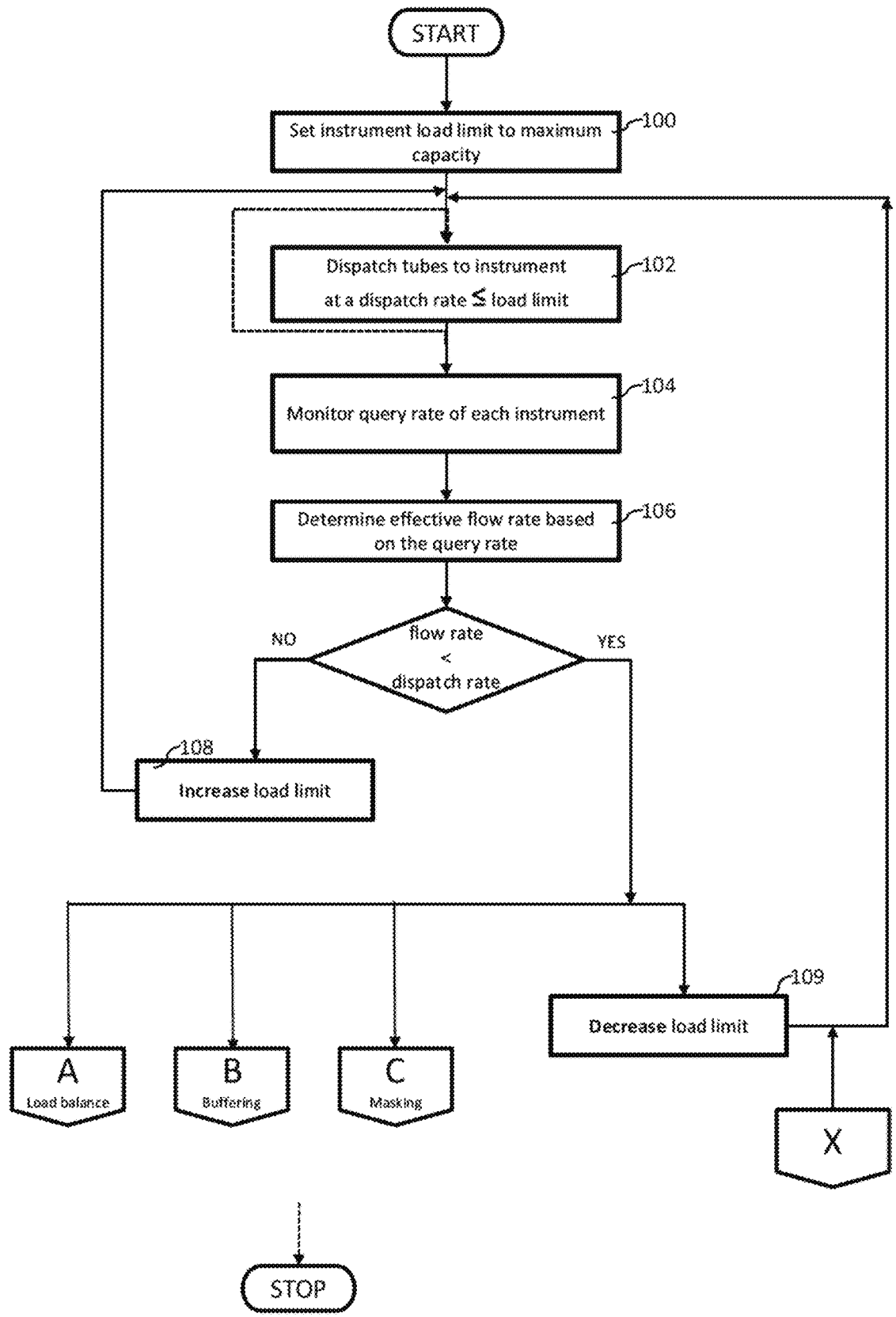
FIG. 4A illustrates a first page of a flowchart illustrating the disclosed methods according to further embodiments of the present disclosure.

FIG. 4A shows a first page of the multi-page flowchart showing steps 100 through 109 (as described above) and off-page connectors A to C, each off-page connector being related to particular embodiments of actions taken by the laboratory middleware 20 in response to the effective flow rate of laboratory instrument(s) 10 deviating from their respective load limits (the effective flow rate of the first laboratory instrument 10) is lower than the corresponding dispatch rate).

Figure 4B:
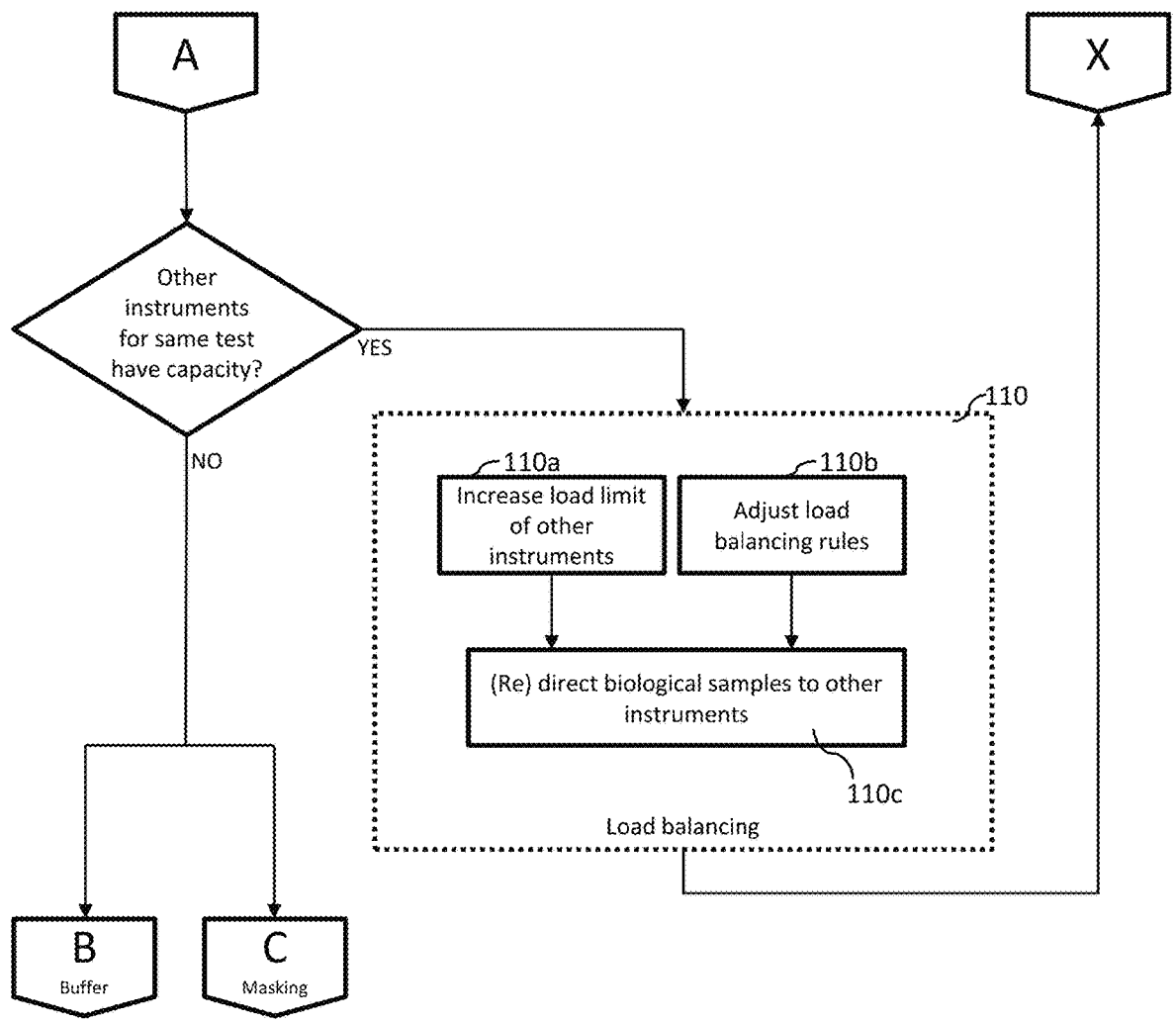
FIG. 4B illustrates a second page of a flowchart illustrating the disclosed method according to further embodiments of the present disclosure.

FIG. 4B shows the second page of the multi-page flowchart illustrating steps from off-page connector A. In order to (re) distribute the workload between laboratory instruments 10 (load balancing—step 110), the laboratory middleware 20 can determine a second laboratory instrument 10 of the plurality of laboratory instruments 10 (other than the first laboratory instrument 10) configured to carry out the same test order corresponding to the respective biological sample as the first laboratory instrument 10. Having determined an alternative instrument to process the biological sample(s), in a step 110a, the laboratory middleware 20 can increase the load limit of the second laboratory instrument 10 by the difference between the effective flow rate and the dispatch rate of the first laboratory instrument 10. To prevent the second laboratory instrument 10 from being overloaded, the laboratory middleware 20 can increase the load limit of the second laboratory instrument 10 up to a value not greater than its maximum instrument capacity. Additionally, or alternatively, in a step 110b, the laboratory middleware 20 can adjust load balancing rule(s) of the laboratory middleware 20 so to decrease the proportion of biological samples dispatched to the first laboratory instrument 10 and increase the proportion biological samples dispatched to the second laboratory instrument 10. A load balancing rule can define the proportion of biological samples sent to each laboratory instrument 10PRE, 10AI, 10POST configured to carry out a particular test order. Thereafter, in a step 110c, the laboratory middleware 20 can redirect samples from the first laboratory instrument 10 to the second laboratory instrument 10 at a rate equal to the difference between the effective flow rate and the dispatch rate of the first laboratory instrument 10. Additionally, or alternatively, the laboratory middleware 20 can dispatch biological samples to the first laboratory instrument 10 and/or to the second laboratory instrument 10 according to the load balancing rule (as adjusted in step 110b).

According to embodiments disclosed herein, in redirecting the biological samples (load balancing), the laboratory middleware 20 can also take into consideration a transportation time of the biological sample(s) to the laboratory instrument 10 the sample is redirected to. The transportation time can be the time required (estimated) to transport the biological sample(s) from the first laboratory instrument 10 to the second laboratory instrument 10 either manually and/or by an automated sample transportation system 10TRS. The calculation/estimation of the transportation time can be based on data indicative of a layout of the sample transportation system 10TRS and/or data indicative of an effective transportation capacity/availability of the sample transportation system 10TRS or a specific transportation route of the sample transportation system 10TRS from the first to the second laboratory instrument. Overall, in optimizing the processing of biological sample(s), the laboratory middleware 20 can monitor and control the load of the sample transportation system 10TRS similarly to other laboratory instruments 10, namely monitoring its effective flow rate and adjusting its load limit (in this case transportation capacity) to avoid overloading and/or underutilization of the sample transportation system 10TRS. In such a way, the overall turn-around-time TAT of the respective biological sample(s) can be significantly improved by ensuring the biological sample(s) are transported to the laboratory instruments 10 as efficiently as possible.

Figure 4C:
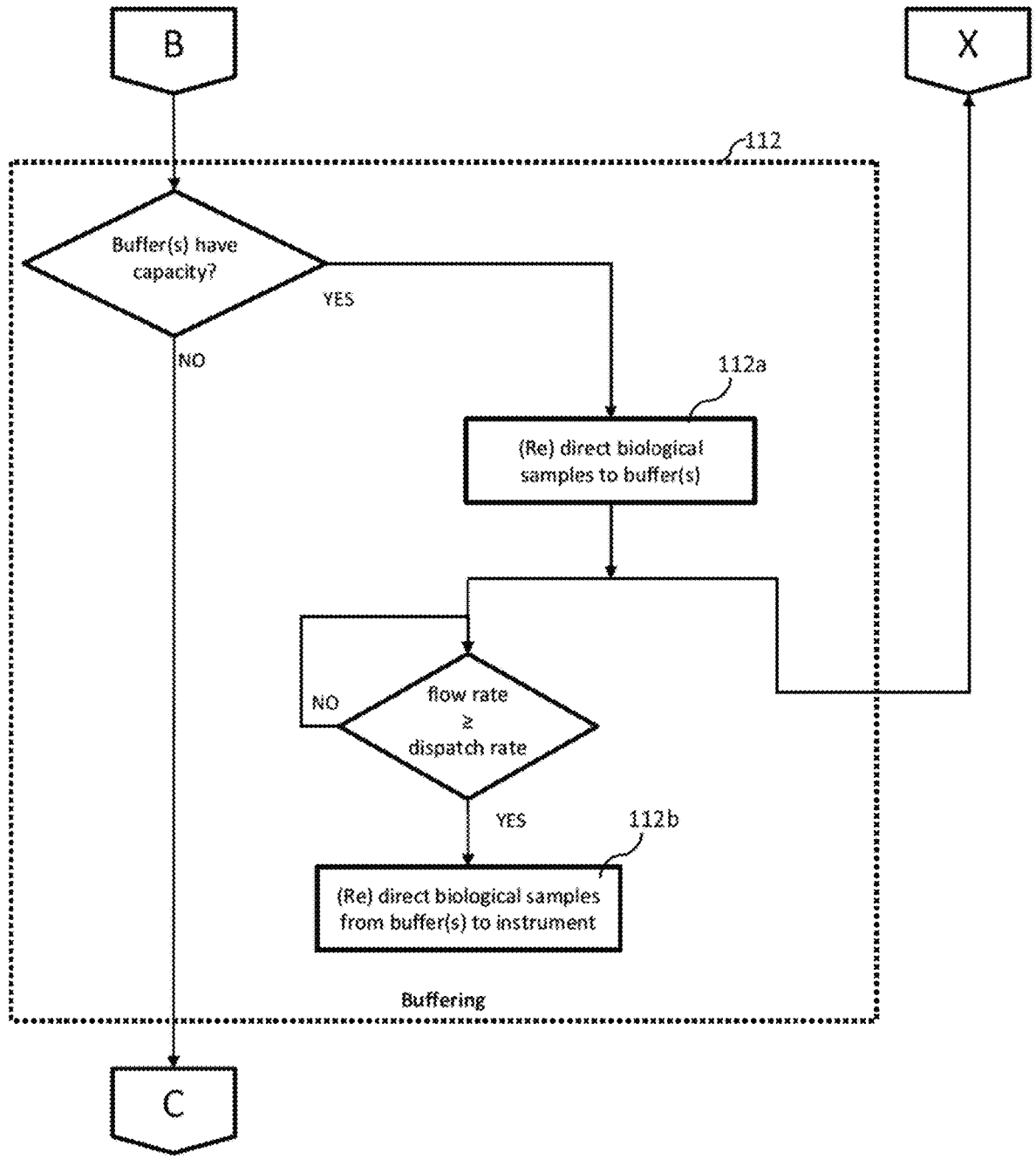
FIG. 4C illustrates a third page of a flowchart illustrating the disclosed method according to further embodiments of the present disclosure.

FIG. 4C shows the third page of the multi-page flowchart illustrating steps from off-page connector B. As illustrated on this figure, alternatively, or additionally, to load balancing (step 110), if the effective flow rate of the first laboratory instrument 10 is lower than the corresponding dispatch rate, the laboratory middleware 20 can buffer biological samples to temporarily reduce the workload of the laboratory instruments 10. In a first step, the laboratory middleware 20 can determine whether any laboratory instrument 10 (referred hereafter as third laboratory instrument) has available buffer capacity. Buffering may be provided either by laboratory instrument dedicated for temporarily storing biological samples and/or by laboratory instruments 10, which have available temporary storage space for biological sample(s) fulfilling the requirements (temperature, humidity) for sample buffering. If there is available buffer capacity, in a step 112a, the laboratory middleware 20 can dispatch biological samples to the third laboratory instrument 10 having available buffer capacity. After dispatching biological sample(s) for buffering, the laboratory middleware 20 can keep monitoring the effective flow rate of the first laboratory instrument 10 and—in a step 112b—can dispatch biological samples from the third laboratory instrument 10 to the first laboratory instrument 10 as soon as the effective flow rate of the first laboratory instrument 10 is equal to or greater than the corresponding dispatch rate. This way, biological sample(s) can be kept in a buffer only as long as needed.

Similarly to load balancing, the laboratory middleware 20 can also take into consideration a transportation time of the biological sample(s) to the third laboratory instrument 10 for buffering. In this way, it can be avoided that biological sample(s) are dispatched for buffering (temporary storage) for periods of time potentially shorter than the time it can take the sample transportation system 10TRS to transport the samples for buffering. Such embodiments can be advantageous since waste of both buffering and transportation capacity can be prevented.

Figure 4D:
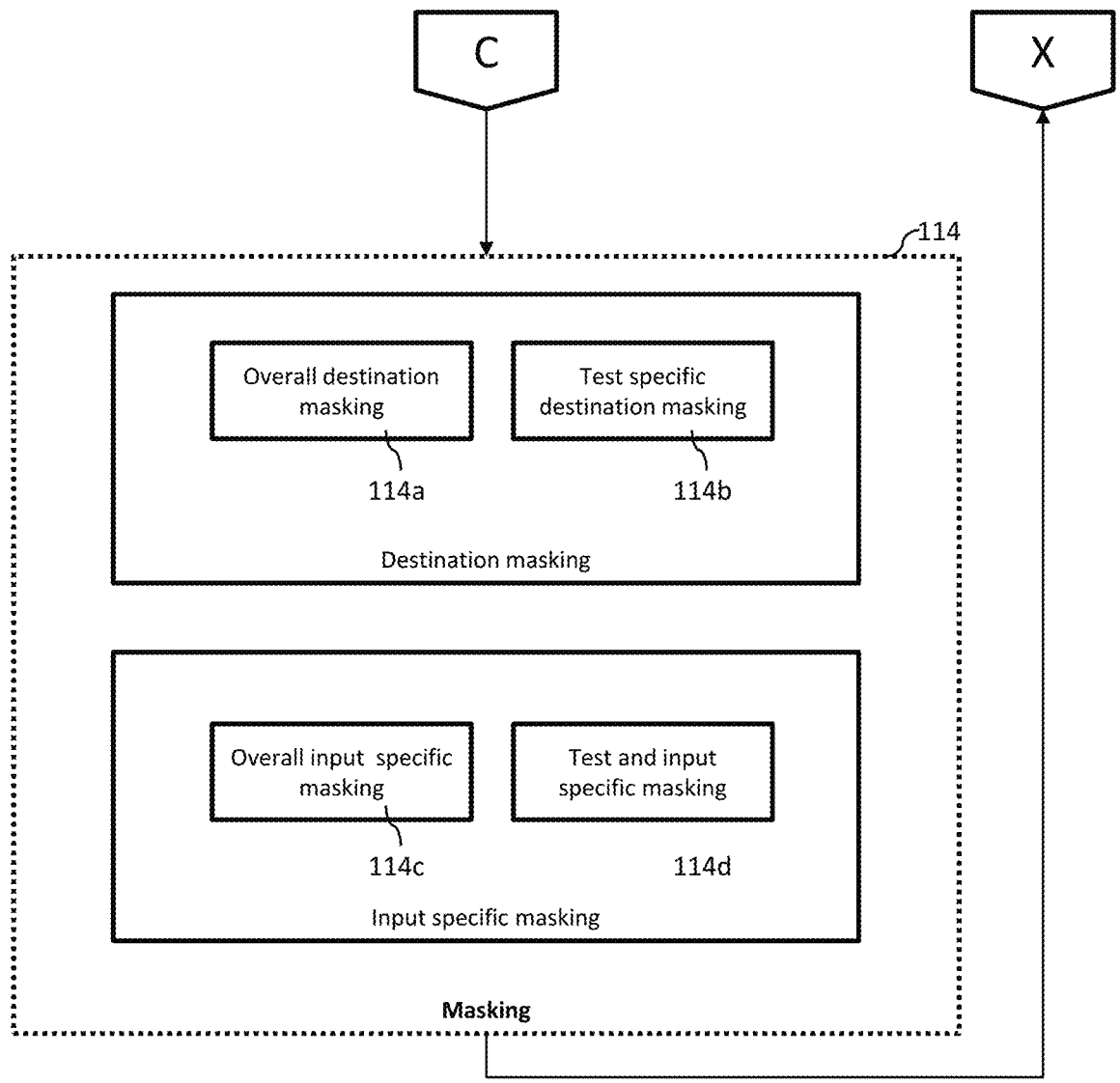
FIG. 4D illustrates a fourth page of a flowchart illustrating the disclosed method according to further embodiments of the present disclosure.

FIG. 4D shows the fourth page of the multi-page flowchart illustrating steps from off-page connector C. FIG. 4D illustrates various methods of a process called instrument masking. Instrument masking, in general, can refer to the process of hiding a particular laboratory instruments 10 from other instruments, as if it would not be available; would be offline; and/or would not exist.

According to embodiments disclosed herein, instrument masking can be ordered into two main categories: destination masking and input specific masking.

Destination masking can refer to the process of preventing one or more of the plurality of laboratory instruments 10 from sending biological sample(s) to the first laboratory instrument 10 (the destination). According to a first embodiment of destination masking (step 114a), referred to as overall destination specific masking, masking can comprise preventing one or more of the plurality of laboratory instruments 10 from sending any biological sample(s) to the first laboratory instrument 10.

In a further embodiment of destination masking, referred to as test specific destination masking—step 114b, masking the first laboratory instrument 10 can comprise preventing one or more of the plurality of laboratory instruments 10 from sending any biological sample(s) having at least one associated test order which the first laboratory instrument 10 is configured to carry out.

Instrument masking can address the need for an analytical laboratory 1 and method of operating an analytical laboratory 1 wherein an overloading of the entire analytical laboratory 1 can be prevented. According to embodiments disclosed herein, preventing one or more of the plurality of laboratory instruments 10 from receiving biological sample(s) can comprise preventing (physically) even the loading of the respective biological sample(s) and/or automatically unloading the biological sample(s), e.g., into an error output. Such embodiments can be advantageous as they can limit the inflow of biological samples into the analytical laboratory 1, thereby preventing that the overall analytical laboratory 1 is overloaded, including buffer and archiving capacity of the laboratory instruments 10.

The second category of instrument masking, input specific masking, can relate to ensuring that the analytical laboratory 1 can still receive and process urgent biological samples while still controlling the overall load of the analytical laboratory 1. In order to achieve this, according to further embodiments, masking of laboratory instruments 10 can be performed with respect to all laboratory instruments 10, other than one or more laboratory instruments 10 reserved for receiving biological samples of high priority. Biological samples may be identified as urgent either by a data marking the biological sample as urgent (STAT sample), the data being read from an identifying label attached to a sample carrier and/or from a data storage unit 22, in particular, as part of the corresponding test order. Alternatively, or additionally, a particular sample tube can identify the biological sample(s) contained therein as urgent. Alternatively, or additionally, any biological sample(s) loaded into a particular laboratory instrument may be designated as urgent, in such case, the respective laboratory instrument being reserved for urgent samples only.

Within input specific masking, two embodiments can be distinguished:
1) Overall input specific masking 114c, wherein one or more of the plurality of laboratory instruments 10 other than the first laboratory instrument 10 and other than one or more laboratory instruments 10 reserved for receiving biological samples of high priority are prevented from receiving any biological sample(s).
2) Test and input specific masking 114d, wherein one or more of the plurality of laboratory instruments 10 other than the first laboratory instrument 10 and other than one or more laboratory instruments 10 reserved for receiving biological samples of high priority are prevented from receiving biological sample(s) having at least one associated test order which the first laboratory instrument 10 is configured to carry out.

Figure 5:
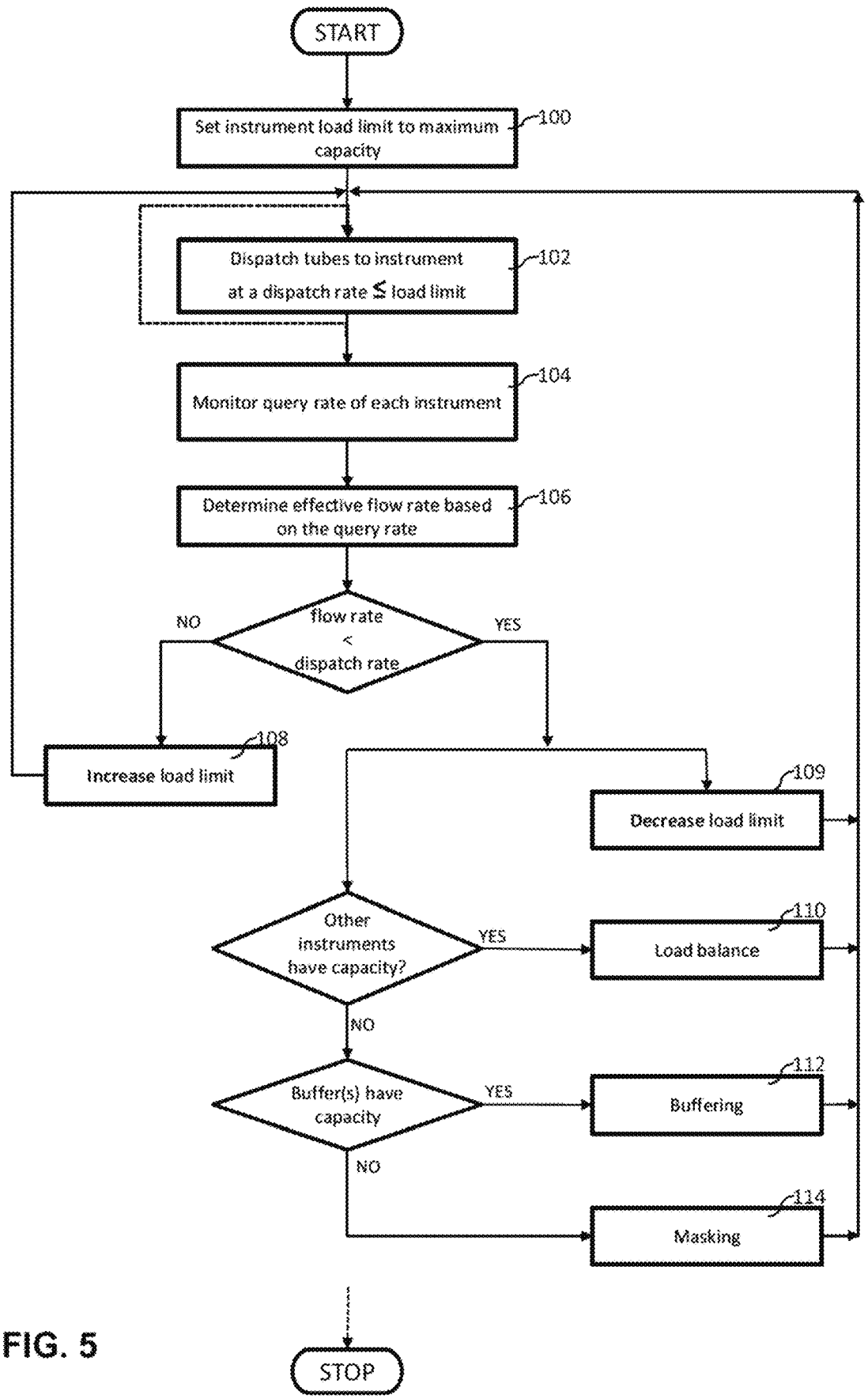
FIG. 5 illustrates a flowchart illustrating an overview of the disclosed method of operating an analytical laboratory according to an embodiment of the present disclosure.

In order to provide an overview of various embodiments of managing the workload and resources of an analytical laboratory 1 by the laboratory middleware 20, FIG. 5 shows a flowchart illustrating load limit control, load balancing, sample buffering as well as instrument masking processes.

Turning now to FIGS. 6-9, particular embodiments of the laboratory instruments 10PRE, 10POST, 10AI are described.

FIG. 6 shows a pre-analytical laboratory instrument 10PRE comprising a sample container sorting unit 14 configured to sort sample containers 30 holding biological samples into sample racks 40, each sample rack 40 being identified by a rack identifier of a rack tag 42 attached to the sample rack 40, the pre-analytical laboratory instruments 10PRE being further configured to transmit signals to the laboratory middleware associating the sample identifier(s) ID of sorted sample containers 30 with the sample rack identifier(s) of the corresponding sample rack(s) 40. For embodiments where a pre-analytical laboratory instrument 10PRE sorts sample containers 30 into sample racks 40, one or more analytical laboratory instruments can be further configured to read the rack identifier Rack-ID from the rack tag 42 and transmit the rack identifier Rack-ID to the laboratory middleware with the test query.

FIG. 7 shows a further embodiment of a pre-analytical laboratory instrument 10PRE, comprising an aliquoting unit 16 configured to prepare aliquots of biological sample(s) from the sample container(s) 30 and provide each of the aliquots with a sample identifier ID on an identifier tag 32 by an identifier tag writer 60.

Figure 8:
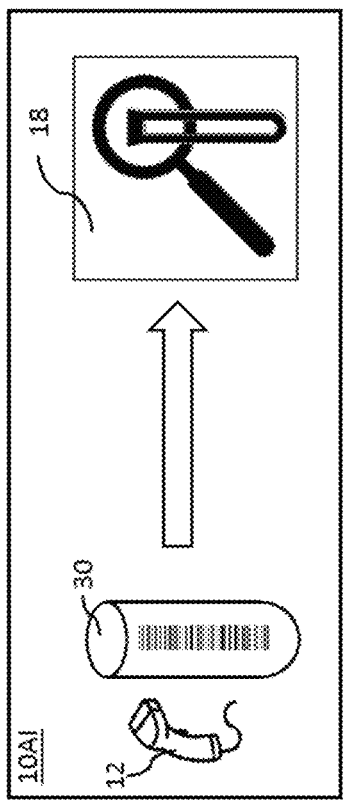
FIG. 8 illustrates a highly schematic block diagram of an analytical laboratory instrument of the disclosed laboratory system according to an embodiment of the present disclosure.

FIG. 8 shows an embodiment of an analytical laboratory instrument 10AI, comprising an analytical unit 18 configured to carry out an analytical test to measure the presence, absence and/or concentration of at least one analyte in the biological sample. The analytical laboratory instrument 10AI can perform analytical test(s) of the biological sample in response to the test order(s).

Figure 9:
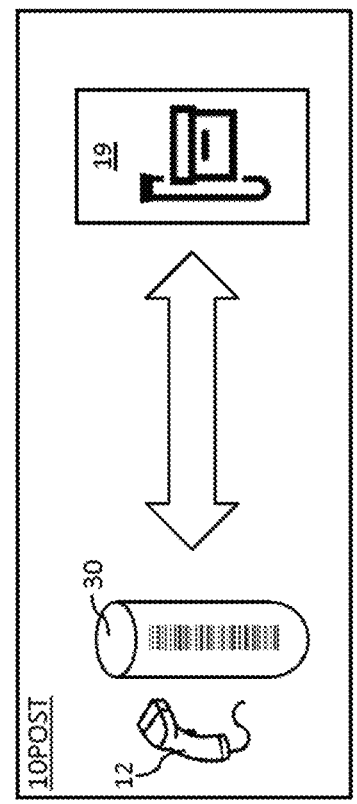
FIG. 9 illustrates a highly schematic block diagram of a post-analytical laboratory instrument of the disclosed laboratory system according to an embodiment of the present disclosure.

FIG. 9 shows an embodiment of a post-analytical laboratory instrument 10POST comprising a sample storage unit 19. The post-analytical laboratory instrument 10AI can be configured to store respectively retrieve sample containers 30 into respectively from the sample storage unit 19. The query by post-analytical laboratory instrument(s) 10POST to the laboratory middleware for a processing order can comprise a container to store respectively retrieve into respectively from the sample storage unit 19. Correspondingly, when queried by a post-analytical laboratory instrument 10POST, the laboratory middleware can transmit data indicative of a sample container 30 to be retrieved from the sample storage unit 19. In response to the data indicative of a sample container 30 to be stored respectively retrieved, the post-analytical laboratory instrument 10POST can store respectively retrieves the sample container 30 from the sample storage unit 19.

Further disclosed is a computer program product comprising instructions which, when executed by a laboratory middleware 20 of an analytical laboratory 1, can cause the analytical laboratory 1 to perform the steps of any one of the methods disclosed herein. Thus, specifically, one, more than one or even all of method steps as disclosed herein may be performed by using a computer or a computer network (such as a cloud computing service) or any suitable data processing equipment. As used herein, a computer program product can refer to the program as a tradable product. The product may generally exist in any format, such as in a downloadable file, on a computer-readable data carrier on premise or located at a remote location (cloud). The computer program product may be stored on a non-transitory computer-readable data carrier; a server computer as well as on transitory computer-readable data carrier such as a data carrier signal. Specifically, the computer program product may be distributed over a data network. Furthermore, not only the computer program product, but also the execution hardware may be located on premise or in a remotely, such as in a cloud environment.

Further disclosed and proposed is a non-transitory computer-readable storage medium comprising instructions which, when executed by a laboratory middleware 20 of an analytical laboratory 1, can cause the analytical laboratory 1 to perform the steps of any one of the methods disclosed herein.

Further disclosed and proposed is a modulated data signal comprising instructions, which, when executed by a laboratory middleware 20 of an analytical laboratory 1, can cause the analytical laboratory 1 to perform the steps of any one of the methods disclosed herein.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating an analytical laboratory comprising a laboratory middleware communicatively connected to a plurality of laboratory instruments configured to process biological samples, the method comprising the steps of:
    setting a load limit by the laboratory middleware for each laboratory instrument at a value equal to a maximum instrument capacity of the laboratory instrument;
    dispatching biological samples by the laboratory middleware to laboratory instrument(s) at a dispatch rate not greater than the instrument load limit, wherein the biological samples are dispatched to laboratory instrument(s) configured to carry out at least one test order corresponding to the biological sample;
    receiving and identifying biological samples by the laboratory instruments;
    sending test order queries by each laboratory instrument to the laboratory middleware upon identifying a biological sample, the test order query comprising data identifying the biological sample;
    in response to the test order queries, transmitting test orders by the laboratory middleware to the laboratory instruments corresponding to the biological samples identified in the test order queries;
    monitoring a query rate of the plurality of laboratory instruments by the laboratory middleware in order to determine an effective flow rate corresponding to each laboratory instrument;
    and
    in response to determining that the effective flow rate of the first laboratory instrument is lower than the corresponding dispatch rate, masking the first laboratory instrument with respect to one or more of the plurality of laboratory instruments other than the first laboratory instrument.

2. The method of operating an analytical laboratory according to claim 1, further comprising,
    checking whether each laboratory instruments have all resources available to process the biological sample according to the test order.

3. The method of operating an analytical laboratory according to claim 2, wherein resources comprise consumables, reagents, quality control, and combinations thereof.

4. The method of operating an analytical laboratory according to claim 1, further comprising,
    checking whether each laboratory instruments is ready to process the biological sample according the test order.

5. The method of operating an analytical laboratory according to claim 1, wherein masking the first laboratory instrument comprises preventing one or more of the plurality of laboratory instruments from sending biological sample(s) to the first laboratory instrument.

6. The method of operating an analytical laboratory according to claim 5, wherein the biological sample(s) have at least one associated test order, which the first laboratory instrument is configured to carry out.

7. The method of operating an analytical laboratory according to claim 5, wherein preventing one or more of the plurality of laboratory instruments from sending biological sample(s) to the first laboratory instrument comprises preventing loading of the biological samples(s) and/or automatic unloading of the biological sample(s).

8. The method of operating an analytical laboratory according to claim 1, wherein all laboratory instruments in the plurality of laboratory instruments are masked except for one or more laboratory instruments reserved for receiving biological samples of high priority.

9. The method of operating an analytical laboratory according to claim 8, wherein biological samples of high priority are identified as high priority by marking the biological sample as urgent on an identifying label attached to a sample carrier and/or a data storage unit.

10. The method of operating an analytical laboratory according to claim 9, wherein the identifying label attached to a sample carrier and/or a data storage unit is read as part of the test order.

11. The method of operating an analytical laboratory according to claim 8, wherein biological samples of high priority are identified as high priority by particular sample tubes containing the biological samples.

12. The method of operating an analytical laboratory according to claim 8, wherein biological samples of high priority are identified as high priority by loading the biological samples into the laboratory instruments reserved only for biological samples of high priority.

13. The method of operating an analytical laboratory according to claim 1, wherein the query rate comprises a number of distinct test order queries received from a laboratory instrument in a set period of time.

14. The method of operating an analytical laboratory according to claim 1, wherein the effective flow rate indicated rate at which the laboratory instrument processes biological samples.

15. The method of operating an analytical laboratory according to claim 1, further comprising, retrieving test orders by the laboratory middleware from a data storage unit based on the data identifying the biological sample.

16. The method of operating an analytical laboratory according to claim 1, wherein the plurality of laboratory instruments are interconnected by a sample transportation system.

17. The method of operating an analytical laboratory according to claim 16, wherein the sample transportation system is a one-dimensional transportation system.

18. The method of operating an analytical laboratory according to claim 17, wherein the sample transportation system is a two-dimensional transportation system.

19. The method of operating an analytical laboratory according to claim 1, wherein masking prevents overloading of the analytical laboratory.

20. The method of operating an analytical laboratory according to claim 1, wherein the plurality of laboratory instruments comprises one or more of analytic instruments, pre-analytical instruments, or post-analytical instruments.

* * * * *